US005422109A

United States Patent [19]

Brancq et al.

[11] Patent Number: 5,422,109
[45] Date of Patent: Jun. 6, 1995

[54] FLUID VACCINES AND ACTIVE PRINCIPLE VEHICLES CONTAINING A METABOLIZABLE OIL

[75] Inventors: Bernard Brancq, Le Chesnay; Gérard Trouve, Castres, both of France

[73] Assignee: Societe d'Exploitation de Produits pour les Industries Chimiques (S.E.P.P.I.C.), Paris, France

[21] Appl. No.: 778,854

[22] PCT Filed: Jun. 29, 1990

[86] PCT No.: PCT/FR90/00485
§ 371 Date: Feb. 28, 1992
§ 102(e) Date: Feb. 28, 1992

[87] PCT Pub. No.: WO91/00107
PCT Pub. Date: Jan. 10, 1991

[30] Foreign Application Priority Data

Jul. 3, 1989 [FR] France .............................. 89 08918

[51] Int. Cl.$^6$ ..................... A61K 39/39; A61K 9/113

[52] U.S. Cl. .............................. 424/184.1; 424/278.1; 424/283.1; 514/785

[58] Field of Search .................... 424/88, 184.1, 278.1; 514/785

[56] References Cited

U.S. PATENT DOCUMENTS

| | | |
|---|---|---|
| 3,983,228 | 9/1976 | Woodhour et al. . |
| 4,069,313 | 1/1978 | Woodhour et al. . |
| 4,795,635 | 1/1989 | Peleg et al. . |
| 4,803,070 | 2/1989 | Cantrell et al. . |

OTHER PUBLICATIONS

Michalek et al (1983) Abstract Only Mol Immunol 20(9):1009–1018.
Yamamoto et al (1978) Abstract Only, Jpn J Med Sci Biol 31(3):263–276.
Yamamoto et al (1978) Abstract Only Jpn J Med Sci Biol 31(56):393–406.
Barteling (Sep. 1980) Abstract Only Tijdschr Diergeneeskd 105(17):695–698.
Francis et al (1983) Abstract Only J Hyg 91(2):329–334.

Al–Dabbass et al., "Immunizing Activity of Oil Adjuvant Attenuated Spore Vaccine of *Bacillus anthracis* in Sheep", *J. Vet. Med.* B 33, 340–345 (1986).

Woodard, L., "Adjuvant Activity of Water–Insoluble Surfactants", *Lab. Animal Sci.,* vol. 39, No. 3, pp. 222–225 (1989).

*Primary Examiner*—Christine M. Nucker
*Assistant Examiner*—Nita M. Minnifield
*Attorney, Agent, or Firm*—Poms, Smith, Lande & Rose

[57] ABSTRACT

The present invention relates to an injectable emulsion, usable as a vaccine or active principle vehicle, which has an oily continuous phase with a good tolerance under normal conditions of injection into a human or an animal, said emulsion being characterized by a viscosity of less than 800 mPas at 20° C. and consisting of at least 20 to 90% of an oily adjuvant which is liquid at 4° C. and contains at least one or more appropriate and pharmaceutically acceptable emulsifiers and a mixture, in any proportions, of one or more metabolizable oils with one or more non-metabolizable oils, and 10 to 80% of a hydrophilic phase containing the active principles or antigens.

13 Claims, No Drawings

FLUID VACCINES AND ACTIVE PRINCIPLE VEHICLES CONTAINING A METABOLIZABLE OIL

The present invention relates to novel compositions of fluid vaccines and injectable substances, containing a totally or partially metabolizable oily phase, which can be used in veterinary or human medicine.

Vaccination is a means of combating infections by prevention, the aim of which is to alert the immune defense system by the injection of antigens, which are often very specific fractions of the viral or bacterial walls.

Advances in genetic engineering are such that the antigens available are more and more pure or even totally synthetic. Although this purity is an undeniable asset from the point of view of the safety of the vaccine, it is generally accompanied by a decrease in the immunological efficacy.

There is therefore an ever-increasing demand for immunity adjuvants making it possible to enhance the responses of the immune system to an antigen. However, the presence of these adjuvants must not compromise the high safety of modern antigen preparations.

A very large number of immunity adjuvants have been described, but only a few of them are used at the industrial vaccine stage and only aluminum hydroxide and phosphate are authorized in human medicine.

It is nevertheless acknowledged that "oily" vaccines, in which the antigen medium is emulsified with a mineral oil containing an emulsifier, are the most effective, especially when these vaccines are of the W/O type.

The adjuvant resulting from the association of mineral oil with a mannitol ester is known as Freund's incomplete adjuvant (FIA) in the literature; it has the following composition:

| fluid mineral oil (Bayol F type): | 85% |
|---|---|
| mannide monooleate (Arlacel A): | 15% |

The difference between FIA and FCA, Freund's "complete" adjuvant, is that the latter contains, in addition to the above-mentioned components, a tuberculin mycobacterium which potentiates the immune effect.

These adjuvants FIA and FCA, which have been known for a long time, are still the reference products for laboratory immunology studies throughout the world.

In particular, they are found associated with novel injectable adjuvants, such as the muramyl dipeptides (MDP), or antigens obtained by chemical or genetic synthesis (VP1, etc.).

The industrial use of vaccines containing FIA and FCA is limited, however, because of the difficulty of using them in injectable vaccine preparations and their poor tolerance by the subjects vaccinated therewith.

In fact, it is known that oily emulsions obtained from FIA and FCA are viscous, like mayonnaise, and release oil. Consequently, these preparations are difficult to inject by means of syringes with a needle of small diameter (0.2 mm).

Furthermore, at the site of injection into animals, they create local reactions with edemas and abscesses, which are not acceptable to the Health Authorities, making the animal unsuitable for human consumption.

Diphtheria vaccine preparations made with FCA have even caused serious intolerances and abortion syndromes when injected into women, which have prohibited the general use of these adjuvants in humans.

An Example of a foot-and-mouth disease vaccine containing FIA is described below in order to demonstrate the immunological efficacy, the physicochemical properties and the poor tolerance of this type of preparation.

EXAMPLE 1

A vaccine preparation for the treatment of foot-and-mouth disease in cattle is made from Freund's incomplete adjuvant (FIA) by mixing one part of FIA and one part of inactivated antigen medium, with mechanical agitation.

The antigen medium was prepared with particular care during the culture, purification and concentration of the antigens, which are diluted in an Eagle-type medium in the presence of phosphate buffer.

The preparation therefore has the following composition (weight/weight):

| Antigen medium | 50% |
|---|---|
| Mineral oil | 42.5% |
| Mannide monooleate | 7.5% |

The physicochemical characteristics obtained for this preparation are as follows:

| Conductivity at 20° C.: | 12 microsiemens |
|---|---|
| Viscosity at 20° C.: | 6500 centistokes |
| pH: | 7.6 |
| Stability: | release of oil on storage at 4° C. |
| Microscopic appearance: | droplets larger than 2 μm |

The immunological efficacy tests on cattle show a good immune response with persistent production of circulating antibodies 30 days after intramuscular vaccination.

Experimental Section

Results of immunity of cattle to foot-and-mouth disease oily vaccines with FIA - dose injected 5 ml the results (EPP) are expressed as the percentage of the number of animals protected against viruses of valencies O, A and C, for a period of 3 months, with vaccines from several batches, stored at 4° C.

TABLE 1

| EPP* | Vaccine n° 1 stored for 1 month at 4° C. | Vaccine n° 2 stored for 24 months at 4° C. |
|---|---|---|
| Virus O 30 days* | 79 | 77 |
| 90 days | 60 | 76 |
| A 30 days | 85 | 80 |
| 90 days | 70 | 69 |
| C 30 days | 93 | 95 |
| 90 days | 72 | 88 |

*measurement of the protection 30 and 90 days after vaccination for determining the prolonged effect of the immunity Microscopic examination of the toxic effects on animals of the vaccine preparation of the point of injection shows the substantial presence of nodules and granulomas and even open abscesses. The extent of the injured regions is considerable.

Histological examination shows the presence of oily residues in the tissues and an appreciable increase in the size of the external ganglia.

To improve the injectability of such oily vaccines, a known technique consists of incorporating a small proportion of a hydrophilic emulsifier, namely polysorbate 80 (described in the pharmacopeias), in the antigen medium.

The presence of this product substantially reduces the viscosity of vaccines, as shown in Example 2.

However, it is known that polysorbate 80, which is used in biochemistry as a lipid dispersant, attacks cell walls and hence is potentially toxic.

EXAMPLE 2

The vaccine preparation made in Example 1 was modified by adding 1% of polysorbate 80 to the FIA.

The composition of the preparation becomes:

| | |
|---|---|
| Antigen medium: | 49.5% |
| Mineral oil: | 42.5% |
| Mannide monooleate: | 7.5% |
| Polysorbate 80: | 0.5% |

The physicochemical characteristics obtained are as follows:

| | |
|---|---|
| Conductivity at 20° C.: | 10 microsiemens |
| Viscosity at 20° C.: | 350 centistokes |
| pH: | 7.6 |
| Stability: | slight ring of oil on storage at 4° C. |

The measurement of the immune response to intramuscular injection in cattle is essentially equivalent to that obtained with the preparation of Example 1 when using a preparation according to Example 2 which was made less than 1 month earlier.

By contrast, when using a preparation according to Example 2 which was made 1 year earlier and has been stored at 4° C. under sterile conditions, it is found that there has been a deterioration in the antigen phase and a decrease in the immune response with a lower titer of circulating antibodies.

These results are explained by the presence of the hydrophilic emulsifier polysorbate 80 (characterized by an HLB of 15), which has a wetting effect on the cellular envelopes of the antigens and solubilizes the surface proteins, the result of which is to denature them and modify their ability to create antibodies.

The mechanism of this effect of hydrophilic surfactants on microorganisms is known and is described in particular in the literature.

As regards the results of toxicity to animals by injection, the phenomena observed are similar to those obtained with the preparation of Example 1 and are characteristic of poor tolerance of the vaccine.

Vaccine preparations made according to the method of Example 2, in which FIA is associated with a hydrophilic emulsifier, are commercially available. Belgian patent A-648053 in the name of Philips describes a brucellosis vaccine which is made under similar conditions and which has an appreciably reduced viscosity compared with the preparations made using FIA alone.

The use of metabolizable oils, such as vegetable oils, squalene and squalane, in place of mineral oils has made it possible in certain cases to obtain vaccines of the W/O type which are tolerated much better. Weilbel et al. only observe small nodules of 3 to 4 mm in humans vaccinated with an influenza vaccine containing peanut oil (Pro. Soc. Exp. Biol. Med. 43, 1053–1056 (1973)), although the immune responses recorded are generally weaker and the protection shorter with this type of vaccine than with vaccines containing mineral oil. This can be explained by a more rapid degradation of the vaccine in the organism.

The Examples reported in British patent 1 081 796 (1965) in the name of L. B. HOLT are very representative of this phenomenon (Table A).

TABLE A

| | Change in the antibody titer with 2 oily vaccines containing FIA or sweet-almond oil as adjuvant | | | | | |
|---|---|---|---|---|---|---|
| | ANTIBODY TITER | | | | | |
| | DIPHTHERIA TOXOID | | TETANUS TOXOID | | B. PERTUSSIS | |
| ANTIGEN | 6 weeks | 13 weeks | 6 weeks | 13 weeks | 6 weeks | 13 weeks |
| ADJUVANT FIA | 0.32 | 0.26 | 5.0 | 0.41 | 20 | 431 |
| vegetable oil + mannide monooleate | 0.10 | 0.07 | 0.30 | 0.20 | 20 | 31 |

Another particularly disadvantageous characteristic of these vaccines containing metabolizable oil is their viscosity, which makes them difficult and painful to inject. The vaccines, containing squalene or squalane as adjuvant, which are described in European patent 0 117 934 have a viscosity greater than 4000 mPas.

Likewise, those described in the article by WOOD-HOUR (Pro. Soc. Exp. Biol. Med. 116, 516–523, 1964), containing peanut oil and aluminum monostearate, are presented as highly viscous water-in-oil emulsions.

It has been found, quite unexpectedly, that the addition of a metabolizable oil to vaccines containing a mineral oil (or, in general, a non-metabolizable oil) makes it possible considerably to improve their tolerance without significantly modifying their immunological efficacy, provided that the vaccines obtained are stable and very fluid.

The use of weakly hydrophilic, non-toxic emulsifiers, obtained from liquid fatty acids, mannitol or glycerol, has made it possible to obtain these totally or partially metabolizable, stable, fluid preparations.

The vaccines (or injectable preparations) of the invention are characterized by 4 important physicochemical parameters:

fluidity: the viscosity, measured by a BROOKFIELD-type viscometer, must be less than 800 centistokes at 20° C. for the vaccine to be injectable through a syringe needle with a diameter of 0.2 mm;

stability: the emulsified preparation must not undergo phase separation, i.e. must not release either the internal antigen phase or the oily phase under storage conditions which are normal for this type of product;

conductivity: this determines the oily or aqueous character of the continuous phase of the emulsion; for values below about 20 microsiemens, an oily continuous phase is obtained at room temperature;

microscopic appearance: the sizes of dispersed droplets of antigen phase are less than 10 μm and distributed over a narrow range.

Apart from the antigen medium or the active principles specific to each injectable preparation, the other constituents (oils, emulsifiers) must satisfy precise criteria defined below.

Definition of the Oil

The fluid oils are selected from mineral, vegetable or animal oils known for their low toxicity. They must be liquid at the storage temperature (+4° C.) or they must at least give liquid emulsions at this temperature. Mineral oils which have a linear chain with more than 16 carbon atoms and are devoid of aromatic compounds will be chosen in particular.

Known examples are MARCOL 52 (produced by ESSO France) and DRAKEOL 6VR (produced by PENRECO USA).

It is also possible to use synthetic mineral oils such as polyisobutenes or polyisoprenes.

particular oleic, linoleic, ricinoleic and cetostearic acids.

It is preferred to use mannitol esters, especially the oleates, obtained under particular conditions of synthesis by dehydrating the polyhydroxylated hydrocarbon chain of mannitol, which cyclizes in the 1–4 or 2–6 positions. The hydrophilicity of the esters obtained can be modified by the grafting of hydrophilic groups such as an alcohol, a polyol, ethylene oxide, propylene oxide, a carboxylic acid, an amine, an amide, etc.

All the emulsifiers used must be pharmaceutically acceptable for use in injectable formulations; in particular, they must be devoid of heavy metals and must have very low acid or peroxide numbers. It is also desirable that they should satisfy the standards of safety tests such as, for example, the one described by S. S. BERLIN (Annals of Allergy 20, 473, 1962).

It is also desirable that the emulsifiers used should form a homogenous, clear and stable phase with the chosen oil, which phase will be emulsified with the aqueous medium appropriate to each injectable preparation.

The emulsifiers described in Table B meet the above demands. They are used in the injectable preparations described in Examples 3 to 9 to form fluid and stable emulsions.

TABLE B

| | Physicochemical characteristics of emulsifiers which can be used in the invention | | | | | |
|---|---|---|---|---|---|---|
| Emulsifier | Reference | 1 | 2 | 3 | 4 | 5 |
| Solubility*   Oil | S | S | S | S | S | S |
| Water | I | D | I | I | I | D |
| HLB (approximate) | 2.6 | 5 | 6.5 | 3 | 2 | 3 |
| Refractive index | 1.4750–1.4765 | 1.4748–1.4758 | 1.4740–1.4750 | — | — | — |
| Hydroxyl number | 89–100 | 90–105 | 90–110 | 87–100 | 20–90 | — |
| Saponification number | 164–172 | 147–160 | 120–140 | 157–170 | 166–186 | — |
| Purity | | | | | | |
| Heavy metals ppm | 20 max. | 20 max. | 20 max. | 20 max. | 20 max. | 20 max. |
| Peroxides mmol/kg | 2 max. | 2 max. | 2 max. | 3 max. | 3 max. | 3 max. |
| Acid number | 1 max. | 1 max. | 1 max. | 1 max. | 3 max. | 2 max. |
| Water % | 2 max. | 2 max. | 2 max. | 2 max. | 2 max. | 2 max. |
| Chemical definition or tradename | Mannide monooleate Montanide 80 (1) | Montanide 888 (1) | Montanide 103 (1) | Montanide 9208 (1) | Mannide dioleate | Purified soya lecithin LIPOID S 75 |

S = Soluble - I = Insoluble - D = Dispersible
(1) registered trademark of SEPPIC France
(2) registered trademark of LIPOID FRG Among the vegetable oils, unsaturated oils rich in oleic acid, which are biodegradable and known for their immunogenic power, will be chosen, examples being peanut oil, olive oil, sesame oil, soy bean oil, wheatgerm oil, etc.

As regards the animal oils, the same criteria of tolerance and immunological efficacy make it possible to use, for example, squalene, squalane and spermaceti oil.

It is advantageous, within the framework of the present invention, to use a mixture of the aforementioned oils.

Definition of the Emulsifier System

The emulsifier system must be adapted to give fluid and stable injectable preparations of the W/O type.

It is composed of one or more surfactants which, when mixed together, have a lipophilic or weakly hydrophilic character with an HLB (hydrophile-lipophile balance) of between 2 and 9.

The emulsifiers are preferably obtained by condensing a fatty acid which is liquid at 20° C. with a sugar (mannitol, glucose, sucrose) or glycerol. The preferred fatty acids are those having at least 16 carbon atoms, in

EXAMPLE 3

This Example shows the importance of the fluidity of the vaccines on their tolerance by animals.

Two AUJESZKY's disease vaccines for pigs are prepared which contain the same antigen medium inactivated with β-propiolactone. The characteristics of vaccine A according to the invention and of vaccine B (containing an adjuvant of the FIA type) are mentioned in Table 3-1. As is apparent from Table 3-1, and as previously described, the range of viscosities is about 37 mPas to 800 mPas.

Vaccine A is characterized by a low viscosity and a good injectability: it contains emulsifier 2 described in Table B.

Both vaccines contain the same fluid mineral oil.

The experiment was performed on 2 groups of 6 pigs to which 2 times 2 ml of vaccine were administered intramuscularly at an interval of 15 days. Serological analysis and histological examination were carried out 59 days after the first vaccination.

The results are collated in Table 8-2. It can be seen from this Table that the antibody titers are similar for the 2 vaccines, but that vaccine A is tolerated much better than vaccine B, for which 2 pigs displayed abnormal behavior after each vaccination. Necroses and suppurations at the sites of injection—which are totally unacceptable to the Health Authorities—are practically absent from group A. The macrophagic granulomas and the inflammatory infiltrates observed are evidence of an intense immune reaction.

TABLE 3 - 1

Characteristics of Aujeszky's disease vaccines for pigs

| | Vaccine A | Vaccine B |
|---|---|---|
| Characteristics of the adjuvant | | |
| Composition | mineral oil: 90% emulsifier 2: 10% | mineral oil: 89% mannide monooleate: 11% |
| Viscosity (mPa · s) | 35 | 40 |
| Refractive index | 1–459 | 1–461 |
| Characteristics of the vaccine | | |
| Composition % w/w | adjuvant: 70 medium: 30 | adjuvant: 50 medium: 50 |
| Viscosity (BROOKFIELD M2V12) | 37 mPa · s | 1870 mPa · s |
| Emulsion type | W/O | W/O |
| Conductivity | 0.2 µS | 0.4 µS |
| Stability at 4° C. | >12 months | >12 months |
| Microscopic appearance | 1 µ drops | 1–5 µ drops |

TABLE 3 - 2

Vaccination results

| | Vaccine A | Vaccine B |
|---|---|---|
| Serology | | |
| Antibody titer (log base 2) (mean over 5 animals) | 2.5 | 2.0 |
| Histology (frequency over 6 pigs) | | |
| Necrosis | 1 | 3 |
| Suppuration | 0 | 3 |
| Fibrosis | 5 | 5 |
| Muscular atrophy | 5 | 6 |
| Macrophagic or lymphocytic granulomas | 5 | 4 |
| Diffuse inflammatory infiltrate | 2 | 2 |
| General reaction | | |
| (modification of behavior) | 0 | 2 |

EXAMPLE 4

A foot-and-mouth disease vaccine for cattle is prepared by mixing one part of adjuvant containing emulsifier 1 and one part of the inactivated antigen medium, with mechanical agitation. The adjuvant contains 5% of a vegetable oil.

The physicochemical characteristics of the adjuvant and of the vaccine obtained are given below (Table 4-1).

The immunological efficacy test gives the results summarized in Table 4-2, which can be compared with the preparation of Example 1.

The activity is maintained in preparations stored for up to 2 years.

The tolerance of the preparation injected intramuscularly into cattle is good. Histological examination reveals a slight inflammation of the tissues at the point of injection, with the presence of only a few nodules and granulomas. Microscopic absorption of the inflammation and microscopic disappearance of the injected product are observed within 15 days of the injection.

TABLE 4 - 1

Characteristics of foot-and-mouth disease vaccine

| Characteristics of the adjuvant | |
|---|---|
| Composition | peanut-oil 5% fluid mineral oil 84% emulsifier 1 11% |
| Appearance | stable, light yellow, clear oily liquid |
| Viscosity | 40 mPa · s |
| Acid number | 0.1 |
| Refractive index | about 1.460 |
| Density | 0.85 |
| Characteristics of the foot-and-mouth disease vaccine | |
| Conductivity at 20° C. | 1.5 microsiemens |
| Viscosity at 20° C. | 250 centistokes |
| Stability at 4° C. | very slight ring of oil |
| Microscopic appearance | droplets smaller than 1 |
| Centrifugation | no separation after 30 min at 3000 rpm |

TABLE 4 - 2

Results of immunity of cattle to foot-and-mouth disease
Dose injected: 5 ml
The results (EPP) are expressed as the percentage of animals protected against viruses of valencies O, A and C for a period of 3 months following vaccination with vaccines from several batches, stored for several months at 4° C..

| EPP | | Vaccine batch n° 3 stored for 1 month | Vaccine batch n° 3 stored for 24 months | Vaccine batch n° 4 stored for 1 month | Vaccine batch n° 4 stored for 3 months |
|---|---|---|---|---|---|
| Virus | 30 d | 90 | 99 | 99 | 90 |
| O | 90 d | 88 | 99 | 99 | 86 |
| Virus | 30 d | 86 | 92 | 97 | 82 |
| A | 90 d | 93 | 90 | 99 | 85 |
| Virus | 30 d | 97 | 99 | 99 | 97 |
| C | 90 d | 92 | 97 | 99 | 85 |

EXAMPLE 5

Mice are vaccinated with vaccines consisting of
an antigen medium containing 100 µg/ml of bovine albumin, and
an oily adjuvant containing either a synthetic oil (vaccine 5A),
or a synthetic oil and a vegetable oil (vaccine 5B).

These two vaccines are fluid and stable. Their physicochemical characteristics are given in Table 5-1.

Groups of 10 SWISS mice are vaccinated with 0.1 ml of these vaccines. A control group receives the antigen medium without adjuvant.

The antibody titers, measured over time by an ELISA technique, are given in Table 5-2. It is found that the two vaccines with adjuvant behave in the same way even though vaccine 5B contains a metabolizable oil, and are distinctly more effective than the vaccine without adjuvant. The rapid appearance of the antibodies with the vaccine containing the metabolizable oil will be noted.

TABLE 5 - 1

Physicochemical characteristics of BSA vaccine

| | Vaccine A | Vaccine B |
|---|---|---|
| Characteristics of the adjuvant | | |
| Composition | polyisobutene: 89% emulsifier 2: 11% | polyisobutene: 44% sweet-almond oil: 45% emulsifier 3: 11% |
| Viscosity (mPa · s) | 45 | 50 |
| Appearance | clear colorless liquid | clear yellow liquid |
| Characteristics of the vaccine | | |

TABLE 5 - 1-continued

Physicochemical characteristics of BSA vaccine

|  | Vaccine A | Vaccine B |
|---|---|---|
| Emulsion type | W/O | W/O |
| Conductivity at 20° C. | 0.9 μS | 1.2 μS |
| Viscosity mPa · s at 20° C. | 100 | 130 |
| Stability | >12 months | >12 months |
| Appearance | homogeneous emulsion | homogeneous emulsion |

TABLE 5 - 2

Antibody titer in mice vaccinated with BSA vaccines

| Days after vaccination | 14 | 28 | 56 | 125 |
|---|---|---|---|---|
| Vaccine without adjuvant | 60 | 157 | 102 | 105 |
| Vaccine 5A | 590 | 2420 | 3800 | 4560 |
| Vaccine 5B | 1400 | 2540 | 3760 | 4640 |

EXAMPLE 6

An injectable preparation containing hormonal active principles is made by mixing one part of an aqueous suspension and one part of an oily adjuvant containing metabolizable oils (squalene and sweet-almond oil: 84%), a non-metabolizable oil (squalane: 5%) and emulsifier 3 (11%).

The vaccine obtained has the following characteristics:

| EMULSION TYPE | W/O |
|---|---|
| CONDUCTIVITY | 0.14 μS |
| VISCOSITY | 305 mPa · s |
| STABILITY at 4° C. and 20° C. | >6 months |

These characteristics, in particular the viscosity and stability, can only be obtained by virtue of the specific formulation of the oily adjuvant. In fact, a vaccine which has the same water/oil ratio but is formulated on the basis of squalene and traditional mannitol monooleate is very viscous (4400 mPas), extremely difficult and painful to inject and of low stability (substantial exudation of oil at 4° and 20° C.).

The preparation according to the invention has a sufficient efficacy and, in primates, causes only slight redness at the point of injection, which disappears after a few days.

EXAMPLE 7

An Aujeszky's disease vaccine is prepared by mixing 30 parts of an inactivated vital medium with a titer of $2.10^9$ DCP 50/ml and 70 parts of an oily adjuvant containing a vegetable oil and emulsifier 3.

Table 7-1 gives the characteristics of the adjuvant and of the vaccine obtained. 2 ml of vaccine are injected into a group of 5 pigs and this is followed by a booster after 15 days. A resistance test is performed 15 days after the booster. Slaughter and histological examination took place 5 weeks after the booster.

The results of the experiment show a very good tolerance of the vaccine in all areas. These results can be compared with those obtained for a conventional oily vaccine containing an adjuvant of the FIA type and presented in Example 3 (vaccine B).

It should be noted in particular that there is an absence of excessive hyperthermia, necroses and suppurations and a presence of discrete macrophagic granulomas, representing the immune response and confirming the good resistance to the infection test.

TABLE 7 - 1

Physicochemical characteristics of the vaccine and its adjuvant

| Characteristics of the adjuvant | |
|---|---|
| Composition | fluid mineral oil 44% |
| | refined peanut oil 44% |
| | emulsifier 1 12% |
| Appearance | homogeneous, stable, clear, straw yellow oily liquid |
| Viscosity at 20° C. | 20 mPa · s |
| Refractive index | 1.466 |
| Hydroxyl number | 13 |
| Saponification number | 105 |
| Characteristics of the vaccine | |
| Emulsion type | W/O |
| Conductivity at 20° C. | 1.9 μS |
| Viscosity at 20° C. | 38 mPa · s |
| Microscopic appearance | homogeneous - 1 μm drops |
| Stability at 4° C. | >12 months |

TABLE 7 - 2

Experimental results of pig vaccination

| Hyperthermia | at the vaccination | 0 |
|---|---|---|
| | at the booster | brief in 2 animals |
| | at the test | intense but brief (<48 h) |
| General reactions | at the vaccination | slight inflammation at the point of injection, disappearing in 48 h |
| | at the booster | |
| | at the test | 0 |
| Mortality (after the test) | | 0 |
| Histology (frequency over 5 pigs) | | |
| Necrosis | | 0 |
| Suppuration | | 0 |
| Fibrosis | | 0 |
| Muscular atrophy | | 5 (slight) |
| Macrophagic granulomas | | 5 (disseminated, discrete) |

EXAMPLE 8

The same experiment as that described in Example 7 was carried out with a vaccine containing 70 parts of an adjuvant composed of squalane, a fatty acid ester and a slightly hydrophilic emulsifier described under reference 2 in Table B, and 80 parts of Aujeszky's antigen medium. The vaccine obtained is very fluid and is easy to inject. Its performance data and characteristics are given in Tables 8-1 and 8-2.

It will again be noted that there is an absence of substantial intolerance reactions compared with the conventional vaccine of Example 1B.

TABLE 8 - 1

Physicochemical characteristics of Aujeszky's disease vaccine for pigs

| Characteristics of the adjuvant | |
|---|---|
| Composition | ethyl oleate 6% |
| | squalane 83% |
| | emulsifier 2 11% |
| Appearance | very light yellow, transparent clear liquid |
| Viscosity at 20° C. | 20 mPa · s |
| Refractive index | about 1.492 |
| Characteristics of the vaccine | |
| Emulsion type | W/O |
| Viscosity at 20° C. | 88 mPa · s |
| Conductivity at 20° C. | 0.03 μS |
| Stability at 4° C. | slight exudation of oil |

TABLE 8 - 2

Experimental results of pig vaccination

| | | |
|---|---|---|
| Hyperthermia | at the vaccination | very slight |
| | at the booster | >41° C., 24 h |
| | at the test | intense but brief |
| General reactions | at the vaccination | 0 |
| | at the booster | slight inflammation at the site of injection |
| | at the test | not pronounced |
| Mortality (after the test) | | 0 |
| Histology (frequency over 5 pigs) | | |
| Caseous abscesses | | 2 |
| Suppuration | | 0 |
| Fibrosis | | 1 |
| Muscular atrophy | | 5 |
| Macrophagic granulomas | | 3 |

TABLE 9

Results of colibacillus vaccination in rabbits

| | days | | | | | |
|---|---|---|---|---|---|---|
| Serology* | 0 | 15 | 24 | booster | 42 | 84 |
| Vaccine of Example 9 | 0 | 9.5 | 11 | ↓ | 11.3 | 10.6 |
| Vaccine with FIA | 0 | 6 | 7 | | 8 | 8 |
| Reactions observed** | days | | | | | |
| | 1 | 4 | 5 | 19 | ↓ 31 | 50 |
| Vaccine of Example 9 | 0 | 20 | 27 | 0 | 35 | 0 |
| Vaccine with FIA | 0 | 30 | 40 | 10 | 60 | 10 |

*Antibody titer expressed as log base 2 of the last agglutinating dilution - geometric mean
**Mean diameters of the erythemas observed (mm) at the point of injection

EXAMPLE 9

A colibacillus vaccine was prepared for vaccination in rabbits.

The antigen medium is a suspension of attachment factor K 88 ab in isotonic solution at a concentration such that the OD of this suspension is 0.5 at 540 nm.

The adjuvant used is the one described in Example 7 and in Table 7-1.

The vaccine contains ⅓ of antigen medium and ⅔ of adjuvant. It has the following characteristics:

| | |
|---|---|
| EMULSION TYPE | W/O |
| CONDUCTIVITY at 20° C. | 2.0 μS |
| VISCOSITY at 20° C. | 40 mPa · s |

6-week-old New Zealand rabbits are vaccinated with 1 ml of vaccine and a booster is then given after 29 days.

The antibody titers are measured by a micro-agglutination technique.

Table 9 gives the results obtained with this vaccine and with a conventional oily vaccine formulated with Freund's incomplete adjuvant (50/50 formula; viscosity > 3000 mPas).

The antibody titers with the vaccine according to the invention are greater than or equal to those measured with the conventional vaccine. The reactions at the site of injection are very substantial with the conventional vaccine, especially after the booster.

They are much weaker and regress more rapidly with the vaccine of the present Example.

EXAMPLE 10

A Newcastle disease vaccine preparation for fowls was made using an adjuvant consisting of

| | |
|---|---|
| DRAKEOL 6VR fluid mineral oil | 82% |
| Soy bean oil | 5% |
| Emulsifier 2 | 13% |

This clear liquid adjuvant has the following characteristics:
Acid number below 0.5
Hydroxyl number of about 11
Refractive index of 1,459

The vaccine is prepared by mixing 7 parts of adjuvant and 3 parts of allantoid medium containing inactivated Newcastle antigens, with mechanical agitation.

The vaccine has the following physicochemical characteristics:

| | |
|---|---|
| Conductivity at 20° C. | below 1 microsiemens |
| Viscosity at 20° C. | 45 centistokes |
| Stability | no release of oil or phase separation of the medium at 4° C. after 3 months |

The preparation also remains stable at 37° C. for more than a week.

Vaccines stored for 12 months at 4° C. and for 1 month at room temperature, as well as a control consisting of the inactivated viral antigens without adjuvant and a live virus vaccine, are injected into the animals.

The study is carried out on 3 series of ten 4-week-old EOPS chickens of the LEGHORN type. The injection is given subcutaneously in the neck region with a dose of 0.5 ml.

The immunological efficacy is measured by titrating the hemagglutination inhibition.

Blood samples are taken from the wing vein of the vaccinated fowl at times Two, 4, 8, 12 and 18 weeks and the hemagglutinin content is measured.

| | Titer of hemagglutination inhibition | | | | |
|---|---|---|---|---|---|
| | Two | 4 wks | 8 wks | 12 wks | 18 wks |
| 1 (control) | 10 | 9 | 10 | 8 | 8 |
| 2 (vaccine according to the invention) | 210 | 230 | 190 | 150 | 160 |
| 3 (live virus vaccine) | 305 | 210 | 120 | 70 | 50 |

It is seen that the immunological activity obtained with the vaccine of the invention is superior to that of the control.

Contrary to what is observed with the live virus vaccine, the activity persists after more than 4 months, which makes it possible to ensure immune protection of chickens against Newcastle disease throughout their life.

From the point of view of toxicity, no mortality of the fowls vaccinated with the vaccine according to the invention is found, whereas a number of chickens (5%) die shortly after injection with the live virus vaccine.

We claim:

1. A parenteral vaccine in the form of an emulsion which comprises on a weight basis:

10 to 80% of a hydrophilic phase containing one or more antigens;

20 to 90% of an oil adjuvant in the form of a homogenous and stable phase which comprises:

one or more metabolizable oils selected from oils of vegetable origin, oils of animal origin, synthetic oil in which the mean number of carbon atoms is at least 16;

one or more non-metabolizable mineral oils representing from 2 to 95% of the oil adjuvant and selected from the group consisting of mineral oils having a mean number of carbon atoms equal to at least 16;

one or more non-toxic, pharmaceutically acceptable emulsifiers which, when mixed together have a lipophilic or weakly hydrophilic character with an HLB (hydrophile-lipophile balance) of between 2 and 9, said emulsifiers being selected from the group consisting of:

mannitol esters;

mannitol esters grafted with hydrophilic groups selected from the group consisting of alcohol, polyol, ethylene oxide, propylene oxide, carboxylic acid, amine and amide; said preparation being stable and having a viscosity of between about 37 mPas to 800 mPas at 20° C. wherein said emulsion provides improved tolerance of said parental vaccine without altering the immunological efficacy of said parenteral vaccine.

2. A preparation according to claim 1, in which the metabolizable oil is of vegetable origin.

3. A preparation according to claim 1, in which the metabolizable oil is of animal origin.

4. A preparation according to claim 1 in which the metabolizable oil is an ester of a fatty acid containing from 12 to 24 carbon atoms and an alcohol, or an ester of a fatty alcohol containing from12 to 24 carbon atoms and an acid.

5. A preparation according to claim 1, wherein said mannitol esters are mannitol oleates.

6. A parenteral vaccine preparation in the form of an emulsion which comprises on a weight basis:

10 to 80% of a hydrophilic phase containing one or more antigens;

20 to 90% of an oily adjuvant in the form of a homogenous and stable phase which comprises:

one or more metabolizable oils selected from the group consisting of oils of vegetable origin, oils of animal origin, synthetic oil in which the mean number of carbon atoms is at least 16;

one or more non-metabolizable mineral oils representing from 2 to 95 % of the oily adjuvant and selected from mineral oils having a mean number of carbon atoms equal to at least 16; and one or more non-toxic, pharmaceutically acceptable emulsifiers which, when mixed together, have a lipophilic or weakly hydrophilic character with an HLB (hydrophile-lipophile balance) of between 2 and 9, said emulsifiers being selected from the group consisting of:

esters of fatty acids and sugar;

esters of fatty acids and sugar grafted with hydrophilic groups selected from the group consisting of alcohol, polyol, ethylene oxide, propylene oxide, carboxylic acid, amine and amide;

esters of fatty acids and glycerol; and esters of fatty acids and glycerol grafted with hydrophilic groups selected from the group consisting of alcohol, polyol, ethylene oxide, propylene oxide, carboxylic acid, amine and amide;

said preparation being stable and having a viscosity of between about 37 mPas and 800 mPas at 20° C. wherein said emulsion provides improved tolerance of said parental vaccine without altering the immunological efficacy of said parenteral vaccine.

7. A preparation according to claim 6, wherein said sugar is selected from the group consisting of mannitol, glucose and sucrose.

8. A preparation according to claim 6, wherein said fatty acid is selected from the group consisting of oleic acid, linoleic acid, ricinoleic acid and cetostearic acid.

9. A preparation according to claim 6, wherein said emulsifiers are selected from the group consisting of mannitol oleates, mannitol oleates grafted with hydrophilic groups, mannitol ricinoleates, mannitol ricinoleates grafted with hydrophilic groups, said hydrophilic groups being selected from the groups consisting of alcohol, polyol, ethylene oxide, propylene oxide, carboxylic acid, amine and amide.

10. A parenteral vaccine preparation in the form of an emulsion which comprises on a weight basis:

10 to 80% of a hydrophilic phase containing one or more antigens;

20 to 90% of an oily adjuvant in the form of a homogeneous and stable phase which comprises:

one or more metabolizable oils selected from oils of vegetable origin, oils of animal origin, synthetic oil of the alkane, alkene or alkyne type in which the mean number of carbon atoms is at least 16;

one or more non-metabolizable mineral oils representing from 10 to 50% of the oily adjuvant and selected from the group consisting of mineral oils having a mean number of carbon atoms equal to at least 16; and one or more non-toxic, pharmaceutically acceptable emulsifiers which, when mixed together, have a lipophilic or weakly hydrophilic character with an HLB (hydrophile-lipophile balance) of between 2 and 9, said emulsifiers being selected from the group consisting of:

esters of fatty acids and sugar;

esters of fatty acids and sugar grafted with hydrophilic groups selected from the group consisting of alcohol, polyol, ethylene oxide, propylene oxide, carboxylic acid, amine and amide;

esters of fatty acids and glycerol; and esters of fatty acids and glycerol grafted with hydrophilic groups selected from the group, consisting of alcohol, polyol, ethylene oxide, propylene oxide, carboxylic acid, amine and amide;

said preparation being stable and having a viscosity of between about 37 mPas and 800 mPas at 20° C. wherein said emulsion provides improved tolerance of said parental vaccine without altering the immunological efficacy of said parenteral vaccine.

11. A preparation according to claim 10, wherein said sugar is selected from the group consisting of mannitol, glucose and sucrose.

12. A preparation according to claim 10, wherein said fatty acid is selected from the group consisting of oleic acid, linoleic acid, ricinoleic acid and cetostearic acid.

13. A preparation according to claim 10, wherein said emulsifiers are selected from the group consisting of mannitol oleates, mannitol oleates grafted with hydrophilic groups, mannitol ricinoleates, mannitol ricinoleates grafted with hydrophilic groups, said hydrophilic groups being selected from the groups consisting of alcohol, polyol, ethylene oxide, propylene oxide, carboxylic acid, amine and amide.

* * * * *